United States Patent [19]

Freiser et al.

[11] 4,399,002
[45] Aug. 16, 1983

[54] LARGE ORGANIC CATION-SELECTIVE ELECTRODES

[75] Inventors: Henry Freiser, Tucson, Ariz.; Charles R. Martin, Austin, Tex.

[73] Assignee: University Patents, Inc., Norwalk, Conn.

[21] Appl. No.: 239,081

[22] Filed: Feb. 27, 1981

[51] Int. Cl.$^3$ ............................................. G01N 27/46
[52] U.S. Cl. ..................................... 204/1 T; 204/418
[58] Field of Search .......... 204/1 T, 1 N, 1 K, 195 R, 204/195 M, 195 L

[56] References Cited

U.S. PATENT DOCUMENTS 3,445,365  5/1969  Ross ................................ 204/195 L
4,115,209  9/1978  Freiser et al. ....................... 204/1 T
4,297,194 10/1981  Dotson et al. ...................... 204/296

OTHER PUBLICATIONS

Analytical Chemistry, vol. 51, No. 8, Jul., 1979, pp. 1328 & 1329.

Analytical Chemistry, vol. 53, No. 6, May, 1981, pp. 902–904.

Primary Examiner—T. Tung
Attorney, Agent, or Firm—George M. Yahwak

[57] ABSTRACT

Concentrations of large organic cationic species in aqueous solution are measured as a function of potentiometric response, employing a cation-selective electrode having a high degree of selectivity for large organic cationic species with respect to both smaller organic cationic species and inorganic cationic species. The electrode is formed with a cation-selective membrane component composed of a polymeric matrix having dispersed or dissolved therein a cation exchange material whose counter-anion is a high molecular weight alkyl or alkaryl sulfonate or sulphate. By proper choice of the cationic moiety of the cation exchange material, the electrode may be made selective for a variety of large organic cationic species, including a number of such species which are of pharmaceutical or clinical interest, thereby enabling potentiometric assays for such species.

22 Claims, No Drawings

LARGE ORGANIC CATION-SELECTIVE ELECTRODES

BACKGROUND OF THE INVENTION

The invention described herein was made in the course of work under a grant or award from the Office of Naval Research.

This invention relates to cation-selective electrodes and, more particularly, to potentiometric assays for large organic cationic species employing such electrodes.

Ion-selective electrodes for use in measuring the concentrations of various ionic species in solutions as a function of potentiometric response, are well known in the art. Such potentiometric assays are typically carried out by simultaneously immersing the ion-selective electrode and a separate reference electrode into the same body of solution to be analyzed, to thereby form an electrochemical cell, across which a potential develops. This potential is proportional to the logarithm of the activity or the concentration in the solution of the ions to which the ion-selective electrode is sensitive. An electrometric device, usually either a direct reading circuit or a null-balance potentiometric circuit, is employed for measuring the potential between the electrodes.

The theoretical relationship between the measured potential and the activity or concentration of a given ionic species in solution for an ion-selective electrode showing exclusive selectivity for the given ionic species, is defined by the well-known Nernst equation, according to which a graphical plot of the negative logarithm of the activity or concentration of a monovalent ionic species sought to be determined versus the measured potential in millivolts, will have a theoretical resultant slope of 59. The relative deviation from this value gives an indication of the degree of selectivity exhibited by the ion-selective electrode employed.

One well-known class of ion-selective electrodes are the membrane electrodes, which employ an ion-selective membrane for interfacing with the test solution to be analyzed. The ion-selective membrane may be formed, for example, of an ion-selective glass material, an ion-selective polymeric material, or an ion-selective water-immiscible liquid. In one type of membrane electrode, commonly referred to as "barrel" electrodes, the ion-selective membrane is in electrical contact with an internal reference electrode element, typically through an internal reference electrolyte solution or fused salt. Barrel-type membrane electrodes employing ion-selective glass membranes, are described in detail in U.S. Pat. Nos. 3,598,713, and 3,502,560; while barrel-type membrane electrodes employing ion-selective polymeric membranes are described in detail in U.S. Pat. Nos. 3,562,129; 3,691,047; and 3,753,887.

A more recently developed type of membrane electrode commonly referred to as "coated wire" electrodes, is described in detail in the Freiser, et. al., U.S. Pat. No. 4,115,209, issued Sept. 19, 1978. In the coated wire-type membrane electrode, an ion-selective polymeric membrane is formed as a layer on a conductive substrate, for example, by forming the membrane as a coating directly on the conductive substrate, which is typically in the form of a conductive wire, thereby eliminating the internal reference electrode element employed in the more conventional barrel-type membrane electrodes.

The membrane electrodes employing ion-selective polymeric membranes offer the greatest flexibility in the list of ionic species to which they could be rendered sensitive, including organic as well as inorganic cationic and anionic species. The ion-selective polymeric membranes are generally composed of a polymeric matrix having dispersed or dissolved therein a suitable ion exchange material, i.e., a cation exchange material for cation sensitivity, and an anion exchange material for anion sensitivity. By proper selection of the ion exchange material present in the membrane component of the electrode, the electrode may be rendered capable of selectively sensing one or more species of cations or anions present in a test solution.

Since many compounds of clinical, pharmaceutical and toxicological interest either are composed of high molecular weight organic cations, or are converted to high molecular weight organic cations at physiological pH values, potentiometric assay techniques employing cation-selective electrodes, potentially offer a more simple, efficient and economical means for assaying for these compounds than many of the analytical techniques typically employed for this purpose, including, for example, mass spectrometry, gas chromatography, liquid chromatography, fluorometry and radioimmunoassay. The primary problem in the practical application of potentiometric assay techniques for this purpose has been in the development of a cation-selective electrode which is capable of exhibiting a sufficiently long operational lifetime in combination with a sufficiently high degree of sensitivity and selectivity for various large organic cationic species with respect to both smaller organic cationic species and inorganic cationic species.

SUMMARY OF THE INVENTION

It is, accordingly, a primary object of the present invention to provide an improved cation-selective electrode for use in measuring the concentration of an organic cationic species in an aqueous test solution as a function of potentiometric response, which is capable of exhibiting a high degree of selectivity for large organic cationic species with respect to both smaller organic cationic species and inorganic cationic species.

Another object of the invention is to provide a cation-selective electrode in accordance with the preceding object, which is capable of exhibiting a high degree of sensitivity for large organic cationic species, thereby enabling the potentiometric detection of such species at low concentration levels.

A further object of the invention is to provide a cation-selective electrode in accordance with the preceding objects, which is capable of exhibiting a relatively long operational lifetime.

Still another object of the invention is to provide a cation-selective electrode in accordance with the preceding objects, which is capable of being employed in potentiometric assays for a number of different large organic cationic species, including such species which are of clinical, pharmaceutical or toxicological interest.

The above and other objects are achieved in accordance with the present invention by providing a cation-selective membrane electrode, wherein the membrane component of the electrode is composed of a polymeric matrix having dispersed or dissolved therein a cation exchange material whose counter-anion is a high molecular weight alkyl or alkaryl sulfonate or sulphate of the formula $R(O)_nSO_3^-$ wherein n is 0 or 1, R is an alkyl group having at least 13 carbon atoms or an alkaryl grop of the formula $R_1$—Ar—$R_2$, Ar is an aryl group, $R_1$ is an alkyl group, and $R_2$ is an alkyl group or H, with the proviso that when Ar is monocyclic and $R_1$ has less than 12 carbon atoms, $R_1$ and $R_2$ are each the same or different alkyl groups having at least 9 carbon atoms, and when Ar is polycyclic and $R_1$ has less than 10 carbon atoms, $R_1$ and $R_2$ are each the same or different alkyl groups having at least 7 carbons atoms.

The cation-selective electrodes of the present invention have a high degree of selectivity for large organic cationic species with respect to both smaller organic cationic species and inorganic cationic species. By proper selection of the cationic moiety of the cation exchange material present in their membrane component, the cation-selective electrodes of the present invention can be rendered highly sensitive to a particular large organic cationic species and can be employed in potentiometric assays for such species which have been found to exhibit near Nernstian response with detection limits as low as about $10^{-6}$ M. Such potentiometric assays may suitably be carried out for a wide variety of different large organic cationic species, including a number of such species which are of clinical, pharmaceutical or toxicological interest, such as, for example, various alkaloidal cations, the protonated form of phencyclidine (PCP), and the protonated form of propranolol. Furthermore, due to the extremely low water-solubility of the counter-anion of the cation exchange material employed therein, the cation-selective electrodes of the present invention have been found to exhibit a relatively long operational lifetime.

DESCRIPTION OF PREFERRED EMBODIMENTS

The present invention resides in the particular cation exchange material employed in the membrane component of a cation-selective polymeric membrane electrode. The invention is applicable to any of the various types and configurations of cation-selective polymeric membrane electrodes which have been described in the prior art as including a cation-selective membrane composed of a polymeric matrix having dispersed or dissolved therein a cation exchange material, the membrane being adapted for interfacing with the test solution to be analyzed and either formed as a layer (e.g., coated or laminated) on a conductive substrate or in electrical contact with an internal reference electrode element.

By way of example, the electrode may be of the "coated wire" type, as described in the Freiser, et. al., U.S. Pat. No. 4,115,209, issued Sept. 19, 1978, incorporated herein by reference to the extent that it is pertinent. In this type of electrode, the cation-selective membrane is formed as a coating directly on a conductive substrate (e.g., copper, platinum, silver, gold, carbon, or the like), which is most conveniently in the form of a fine wire. Alternatively, the electrode may be of the more conventional type employing an internal reference electrode element (e.g., a silver/silver chloride electrode) in electrical contact with the membrane (e.g., through an internal reference electrolyte solution in either liquid or solid form, or through a fused salt layer). Examples of these types of electrodes are described in detail in the Simon U.S. Pat. No. 3,562,129, issued Feb. 9, 1971; the Ross, et. al., U.S. Pat. No. 3,691,047, issued Sept. 12, 1972; the Kedem, et. al., U.S. Pat. No. 3,753,887, issued Aug. 21, 1973; and the Battaglia, et. al, U.S. Pat. No. 4,214,968, issued July 29, 1980; all of which are incorporated herein by reference to the extent that they are pertinent.

The cation exchange material employed in the cation-selective polymeric membrane component of the electrodes in accordance with the present invention, has as its counter-anion a high molecular weight alkyl or alkaryl sulfonate or sulphate of the formula $R(O)_nSO_3^-$, wherein n is 0 or 1, and R is an alkyl group having at least 13 carbon atoms or an alkaryl group as defined above. The counter-anion is preferably an alkaryl sulfonate (i.e., wherein n is 0 and R is an alkaryl group), such as an alkylated benzene sulfonate or an alkylated naphthalene sulfonate. Monoalkyl benzene sulfonates can be employed, provided that the alkyl group has at least 12 carbon atoms. Otherwise, the alkylated benzene sulfonate will be a dialkyl benzene sulfonate, wherein the two alkyl groups, which may be the same or different, will each have at least 9 carbon atoms. Similarly, monoalkyl naphthalene sulfonates may be employed provided that the alkyl group has at least 10 carbon atoms. Otherwise, the alkylated naphthalene sulfonate will be a dialkyl naphthalene sulfonate, wherein the two alkyl groups, which may be the same or different, will each have at least 7 carbon atoms. Particularly preferred cation exchange materials for use in the present invention are those whose counter-anion is either dinonylnaphthalene sulfonate or didodecylnaphthalene sulfonate.

The cationic moiety of the cation exchange material present in the membrane component of the cation-selective electrodes of the present invention will generally comprise the particular cationic species for which the electrode is to be rendered sensitive. While such cationic species may, if desired, be either inorganic or organic in nature, or of any desired molecular size, the maximum benefits obtainable from the utilization of the present invention will be realized when such cationic species is a large organic cationic species. Of particular suitability in this regard, are the large organo-substituted ammonium cations, including quaternary ammonium cations, as well as protonated tertiary amines, protonated secondary amines, and protonated primary amines.

Suitable large quaternary ammonium cations include, for example, tetrapropyl ammonium, tetrabutyl ammonium, tetrapentyl ammonium, tetrahexyl ammonium, decyltrimethyl ammonium, and dodecyltrimethyl ammonium cations. Suitable large protonated amines include the protonated forms of a number of compounds of clinical, pharmaceutical or toxicological interest, such as, for example, the protonated form of phencyclidine (PCP), the protonated form of propanolol, and the various alkaloidal cations, including the protonated forms of morphine, cocaine, heroin, atropine, nicotine, quinine, strychnine, dextromethorphan, diphenhydramine, promazine, phenindamine, mecloxamine, dicyclomine, and the like.

The polymeric matrix of the membrane component of the cation-selective electrodes in accordance with the present invention, may be formed of any suitable polymeric material including, for example, addition polymers, such as the vinyl polymers, including polyvinyl chloride, polyvinylidene chloride, polyethylene, polypropylene, polybutadiene, polyacrylamides, polyacrylates, polyvinyl acetate, chloroprene, polystyrenes, polyacrylonitrile, and the like; condensation polymers, such as polyamides, polycarbonates, polyurethanes, polyesters, polyethers, and the like; and natural resins such as purified natural rubber.

The membrane will generally include the cation exchange material in amounts ranging from about 1 to about 25% by weight and preferably from about 5 to about 25% by weight. A plasticizer for the polymer, compatible with both the polymer and the cation exchange material, may be included within the membrane to attain a more homogeneous mixture of the cation exchange material with the polymeric material. Suitable plasticizers which may be used, depending upon the particular polymer employed, include cyclohexanone, dioctyl phosphonate, tributyl phosphate, isoamyl alcohol, n-decanol, dipentylphthalate, dioctylphthalate, and diphenylphthalate. When a plasticizer is used, it will generally be employed in an amount ranging from about 10 to about 50% by weight of the membrane.

The membrane may suitably be prepared by first forming a homogeneous solution of the cation exchange material, the polymer, and the optional plasticizer, in a suitable organic solvent, such as, for example, an alcohol (e.g., isoamyl alcohol, benzyl alcohol, or decanol), a ketone (e.g., cyclohexanone), an ester (e.g., methyl acetate, or tributyl phosphate), or a cyclic ether (e.g., tetrahydrofuran). Such solution is then either cast into a disk or coated onto a suitable substrate depending upon the type of electrode being prepared, and the solvent is then evaporated.

The cation exchange material may be in its desired cationic form prior to membrane preparation. Alternatively, the membrane may be prepared with the cation exchange material in its $H^+$ form, and subsequently converted into the desired cationic form by soaking the membrane in a dilute solution of an appropriate salt of the desired cationic species.

The cation-selective electrodes of the present invention may suitably be employed, in accordance with conventional assaying techniques well known in the art, either for direct potentiometric assays or as indicator electrodes in potentiometric titrations, for measuring the concentration of a number of different large organic cationic species, including many of such species which are of clinical, pharmaceutical or toxicological interest, in various aqueous test solutions, including biological fluids such as blood, plasma, serum, urine, and the like. The electrodes have been found to exhibit a high degree of selectivity for large organic cationic species with respect to both smaller organic cationic species and inorganic cationic species, with the selectivity sequence being determined by solvent extraction principles. The electrodes have also been found to exhibit a high degree of sensitivity for various large organic cationic species, with detection limits as low as about $10^{-6}$ M. The electrodes have furthermore been found to exhibit a relatively long operational lifetime in comparison with previously proposed organic cation-selective electrodes. Such improved operational lifetime is believed to be primarily due to the extremely low water-solubility of the high molecular weight counter-anions of the cation exchange material employed in the membrane component of the electrodes, and the resulting reduced tendency for the cation exchange material to leach out of the electrode.

The invention is further illustrated by way of the following examples.

EXAMPLE 1

Cation-selective polymeric membrane electrodes, of both the coated wire (CWE) type and the conventional barrel type, were prepared with polymeric membranes composed of 50 weight percent polyvinyl chloride, 45 weight percent dioctyl phthalate, and 5 weight percent dinonylnaphthalene sulfonic acid (DNNS). The membranes were formed by adding the other two components to a 5 (w/v) percent solution of the polyvinyl chloride in tetrahydrofuran, and then using the resulting solution to either cast membrane disks for the barrel type electrodes, or coat copper wires for the CWE's. The DNNS in the membranes thus prepared was converted into either the $Na^+$ form, the tetrabutyl ammonium (TBA$^+$) form, or the dodecyltrimethyl ammonium (DoTA$^+$) form by soaking in either a $10^{-3}$ M (TBA$^+$ and DoTA$^+$) or a $10^{-2}$ M (Na$^+$) solution of the appropriate salt. Soaking times of from one to two days were employed. The Na$^+$ membranes were used in electrodes only of the barrel type, the TBA$^+$ membranes were used in electrodes of only the CWE type, and the DoTA$^+$ membranes were used in electrodes of both the barrel and CWE types. The barrel type electrodes employed a Ag/AgCl reference electrode, and a $10^{-3}$ M solution of the appropriate salt as the internal reference electrolyte solution. When not in use, the electrodes were stored in a $10^{-3}$ M solution of the appropriate salt.

All electrode potentials were measured vs. a double junction Ag/AgCl reference electrode, with 0.1 M NH$_4$NO$_3$ being used in the external junction. Calibration experiments were carried out using a microcomputer-controlled potentiometric analysis system. The electrodes were repeatedly calibrated over a period of at least one month. Least squares analysis of the potential vs. log activity data thus obtained was then used to determine average slope and standard deviation values for each electrode. Ion size parameters for the symmetrical quaternary ammonium ions were obtained from Petrucci, "Ionic Interactions from Dilute Solutions to Fused Salts," volume I, page 43, Academic Press: New York 1971. Based on these ion-sized parameters, DoTA$^+$ and decyltrimethyl ammonium (DTA$^+$) were assigned an approximate ion size parameter of $6 \times 10^{-8}$ cm. Selectivity coefficients were determined by a modified form of the mixed solutions method described by Srinivasan and Rechnitz, Anal. Chem., 41, 1203 (1969).

The critical response characterisitics for the various DNNS-based electrodes are summarized in Table I. The data indicate that a nearly Nernstian response to TBA$^+$ and DoTA$^+$ is obtained over three orders of magnitude in concentration. The linear response of the DoTA$^+$ electrode is limited at higher concentrations by micelle formation. The critical micelle concentration is about $10^{-2}$ M. Above this concentration flattening of the calibration curve is observed which does not represent a failure of the electrode to function properly, but rather represents the complex solution chemistry that results from micelle formation. Although no evidence for micelle formation was observed with the TBA$^+$ electrode, some minor concave curvature of the calibration curve occured for concentrations above $10^{-2}$ M. While this curvature at higher concentrations is difficult to explain, it does not prohibit the use of the electrode at these concentrations. Hence, a useable range to $10^{-1}$ M is reported in Table I. The lower limit of the useable range for each electrode shown in Table I is based on the detection limit recommended by IUPAC Comp. Anal. Nomenclature, pages 168-169, Pergamon Press: New York, 1977. As the data indicate, the sensitivities of both the TBA+ and DoTA+ electrodes are very good. Selectivity coefficients ($K_{sel}$) for the various electrodes are presented in Table II. These data show that DNNS has great selectivity for large organic cations. Both the TBA+ and DoTA+ electrodes exhibit negligible interference from inorganic cations. Indeed, to obtain a measurable potential difference between solution 1 (pure DoTA+ or TBA+) and solution 2 (DoTA+ or TBA+ and interfering cation) a concentration of the primary ion as low as $10^{-5}$ M and an interfering ion concentration as high as 0.09 M had to be used. The selectivity data also demonstrate the dominate role played by solvent extraction parameters in determining the selectivity characteristics of the electrode. In general, the selectivity coefficients for monovalent ions increase with the atomic or molecular weight of the ion for all of the electrodes tested.

In the following tables, "ISE" denotes ion selective electrode, and "Conventional" refers to the barrel type electrode.

$10^{-3}$ M acetate buffer. This same solution was employed as the internal reference electrolyte solution in the electrode, as well as for storing the electrode when not in use.

The critical response characteristics of the resulting DNNS-based PCP+ electrode are summarized in Table III. The highest concentration of PCP-HCl used for calibration was $10^{-3}$ M; it was not considered necessary to calibrate to higher concentrations. As the data indicate, nearly Nernstian response was obtained down to $10^{-4.2}$ M.

The selectivity coefficients ($k_{ij}$) for the PCP+ electrode are presented in Table IV. The selectivity data indicate negligible interference from inorganic cations, as well as the role played by solvent extraction parameters in determining selectivity in that the selectivity coefficients for the monovalent ions increase with the molecular weight of the ion.

TABLE I

Critical Response Characteristics of DNNS-Based Electrodes.

| | Ion | | | |
| | | | DoTA+ | |
| Parameter | Na+ | TBA+ | CWE | Conventional |
|---|---|---|---|---|
| Slope (MV/log a) | $-56.04 \pm .17^a$ | $-59.99 \pm 0.30^a$ | $-59.04 \pm 0.35^a$ | $-59.13 \pm .31^a$ |
| Standard Deviation[b] (MV/log a) | .265 | 0.299 | 0.158 | .134 |
| Linear Range (M) | $10^{-2}-10^{-4c}$ | $10^{-2}-10^{-5}$ | $10^{-2}-10^{-5}$ | $10^{-2}-10^{-5}$ |
| Useable Range (M) | | $10^{-1}-10^{-5.8}$ | $10^{-2}-10^{-6.2}$ | $10^{-2}-10^{-5.9}$ |

[a]Standard deviation in slopes obtained for multiple calibrations.
[b]Average of standard deviations obtained from least squares analyses of individual calibration curves.
[c]The Na+ electrode was calibrated only over this range.

TABLE II

Selectivity Coefficients for the DNNS-Based Electrodes.

| | | | DoTA+-ISE | |
| Interferants | Na+-ISE | TBA+-ISE | CWE | Conventional |
|---|---|---|---|---|
| DoTA+[b] | $>10^{5a}$ | 5.3 | (1) | (1) |
| TBA+[c] | $>10^{5a}$ | (1) | .18 | .21 |
| DTA+[d] | | 0.54 | .084 | .085 |
| TPA+[e] | | 0.02 | .031 | .038 |
| TEA+[f] | $4.7 \times 10^3$ | $4.4 \times 10^{-4}$ | $1.1 \times 10^{-4}$ | $1.5 \times 10^{-4}$ |
| TMA+[g] | 30 | $1.2 \times 10^{-4}$ | $<10^{-4}$ | $<10^{-4}$ |
| Ag+ | 22 | | | |
| K+ | 6.5 | $<10^{-4}$ | $<10^{-4}$ | $<10^{-4}$ |
| NH4+ | 3.1 | $<10^{-4}$ | $<10^{-4}$ | $<10^{-4}$ |
| Na+ | (1) | $<10^{-4}$ | | |
| Li+ | 0.76 | | $<10^{-4}$ | $<10^{-4}$ |
| H+ | 0.46 | $<10^{-4}$ | $<10^{-4}$ | $<10^{-4}$ |
| Pb2+ | | $<10^{-4}$ | $<10^{-4}$ | $<10^{-4}$ |
| Ca2+ | | $<10^{-4}$ | $<10^{-4}$ | $<10^{-4}$ |
| Mg2+ | 0.69 | $<10^{-4}$ | $<10^{-4}$ | $<10^{-4}$ |

[a]$K_{sel}$ varies greatly with concentrations of primary and interfering ions.
[b]Dodecyltrimethylammonium
[c]Tetrabutylammonium
[d]Decyltrimethylammonium
[e]Tetrapropylammonium
[f]Tetraethylammonium
[g]Tetramethylammonium

TABLE III

| Critical Response Characteristics of DNNS-based PCP+ Electrode. | |
|---|---|
| Slope (mV/log a) | $59.21 \pm 0.59^a$ |
| Standard deviation (mV)[b] | 0.091 |
| Intercept (mV) | $392.41 \pm 1.80^c$ |
| Lower limit of linear range (M) | $10^{-4.2}$ |
| Detection limit (M) | $10^{-5.1}$ |

[a]Standard deviation in slopes obtained for multiple calibrations over 30 day period.
[b]Average of standard deviations obtained from least squares analyses of individual calibration curves.
[c]Standard deviation in intercept obtained for multiple calibration.

TABLE IV

| Selectivity Coefficients for the DNNS-based PCP+ Electrode. | |
|---|---|
| Interferants | $k_{i,j}$ |
| Mg2+ | $<10^{-4}$ |
| Ca2+ | $<10^{-4}$ |
| H+ | $<10^{-4}$ |
| Na+ | $<10^{-4}$ |
| K+ | $<10^{-4}$ |
| TMA+[a] | $1.4 \times 10^{-4}$ |
| TEA+[b] | $8.6 \times 10^{-4}$ |
| TPA+[c] | 0.031 |
| DTA+[d] | 0.68 |
| TBA+[e] | 1.7 |
| DoTA+[f] | 7.1 |

[a]Tetramethylammonium
[b]Tetraethylammonium
[c]Tetrapropylammonium
[d]Decyltrimethylammonium
[e]Tetrabutylammonium
[f]Dodecyltrimethylammonium

EXAMPLE 2

The procedure of Example 1 was repeated to prepare a cation-selective polymeric membrane electrode of the conventional barrel type with the DNNS in the polymer membrane being converted to the PCP+ (the protonated form of phencyclidine) form by soaking the electrodes for two days in $10^{-3}$ M phencyclidine-hydrochloride (PCP-HCl) buffered at pH 5.0 with

EXAMPLE 3

The procedure of Example 1 was repeated, to prepare cation-selective polymeric membrane electrodes of both the coated wire and conventional barrel types, wherein the DNNS in the membrane was replaced with didodecylnaphthalene sulfonic acid (DDNS), which was converted to the propranolol-DDNS ion-pair form by soaking the electrodes for one week in $10^{-3}$ M propranolol-HCl buffered at pH 5.0 with $10^{-2}$ M acetate buffer. This same solution was employed as the internal reference electrolyte solution of the conventional barrel-type electrode, as well as for storing the coated wire electrode when not in use. The storage solution used for the barrel type electrode was $10^{-4}$ M in propranolol.

The response characteristics of the DDNS-propranolol electrodes are summarized in Table V. Both of these electrodes exhibited a linear, nearly Nernstian response down to $10^{-5}$ M with a lower limit of detection at approximately $10^{-6}$ M. It should be pointed out that at the lower concentrations, the electrodes should be equilibrated for 30 minutes to obtain the proper response. Although the conventional barrel-type electrode has a somewhat greater sensitivity than the CWE, the response times of the latter are significantly faster. It should be noted that the reproducibility measures reported in Table V, represent averages of data obtained from at least 8 electrodes collected over a period of a month, demonstrating the high stability and reproducibility of these electrodes.

The selectivity ratios ($K_{ij}$) of the propranolol electrodes are shown in Table VI. The selectivity data indicate negligible interference from common inorganic cations, indicating that the determination of propranolol in physiological fluids can be readily accomplished using these electrodes. Furthermore, the $K_{ij}$ of 1-isoproterenol, a di-hydroxylated analog of isopropranolol, is small enough so that it will not provide significant interference. The propranolol electrodes were found to still be performing well and having essentially unchanged operating parameters after over six months.

TABLE V

Critical Response Characteristics of Propranolol Electrodes.

| | Type | |
|---|---|---|
| | Coated Wire | Conventional |
| Slope (mV/log a)[a] | 59.51 ± 0.71 | 59.70 ± 0.42 |
| Standard deviation (mV)[b] | 0.11 | 0.16 |
| Intercept (mV)[c] | 528 ± 12 | 392.6 ± 5.1 |
| Lower limit of linear range (M) | $10^{-5.00}$ | $10^{-5.40}$ |
| Detection limit (M) | $10^{-5.80}$ | $10^{-6.00}$ |

[a]Standard deviation in slopes obtained for multiple calibrations over 30 day period.
[b]Average of standard deviations obtained from least squares analysis of individual calibration curves.
[c]Standard deviation in intercept obtained for multiple calibration.

TABLE VI

Selectivity Ratios for Propranolol Electrodes

| | Type | |
|---|---|---|
| Interference | Coated Wire $K_{ij}$ | Conventional $K_{ij}$ |
| $Mg^{2+}$ | $<10^{-4}$ | $<10^{-4}$ |
| $Ca^{2+}$ | $<10^{-4}$ | $<10^{-4}$ |
| $K^+$ | $<10^{-4}$ | $<10^{-4}$ |
| $NH_4^+$ | $<10^{-4}$ | $<10^{-4}$ |
| $H^+$ | $-2.2 \times 10^{-4}$ | $1.3 \times 10^{-4}$ |
| Dimethylammonium | $2.4 \times 10^{-4}$ | $2.1 \times 10^{-4}$ |
| Dipropylammonium | 0.026 | 0.036 |
| Dibutylammonium | 0.31 | 0.32 |
| Triethylammonium | $3.2 \times 10^{-3}$ | $4.6 \times 10^{-3}$ |
| Tripropylammonium | 0.042 | 0.072 |
| Tributylammonium | 4.0 | 5.8 |
| Tetramethylammonium | $1.1 \times 10^{-3}$ | $1.8 \times 10^{-3}$ |
| Tetraethylammonium | 0.010 | 0.017 |
| Tetrapropylammonium | 0.90 | 1.9 |
| Tetrabutylammonium | 49 | 120 |
| Decyltrimethylammonium | 19 | 29 |

TABLE VI-continued

Selectivity Ratios for Propranolol Electrodes

| | Type | |
|---|---|---|
| Interference | Coated Wire $K_{ij}$ | Conventional $K_{ij}$ |
| Dodecyltrimethylammonium | 130 | 170 |
| 1-Isoproterenol | $2.6 \times 10^{-3}$ | $1.5 \times 10^{-3}$ |

The embodiments of the invention in which an exclusive property or privilege is claimed are defined as follows:

1. In a cation-selective electrode for use in measuring the concentration of an organic cationic species in an aqueous test solution as a function of potentiometric response, comprising a cation-selective membrane adapted for interfacing with said test solution and either formed as a layer on a conductive substrate or in electrical contact with an internal reference electrode element, said membrane being composed of a polymeric matrix having dispersed or dissolved therein a cation-exchange material, the improvement which comprises said cation exchange material having as its counter-anion a high molecular weight alkyl or alkaryl sulfonate or sulfate of the formula $R(O)_nSO_3^-$, wherein n is 0 or 1, R is an alkyl group having at least 13 carbon atoms or an alkaryl group of the formula $R_1$—Ar—$R_2$, Ar is an aryl group, $R_1$ is an alkyl group, and $R_2$ is an alkyl group or H, with the proviso that when Ar is monocyclic and $R_1$ has less than 12 carbon atoms, $R_1$ and $R_2$ are each the same or different alkyl groups having at least 9 carbon atoms, and when Ar is polycyclic and $R_1$ has less than 10 carbon atoms, $R_1$ and $R_2$ are each the same or different alkyl groups having at least 7 carbon atoms, whereby said electrode has a high degree of selectivity for large organic cationic species with respect to both smaller organic cationic species and inorganic cationic species.

2. The cation-selective electrode of claim 1, wherein said counter-anion of said cation exchange material is an alkaryl sulfonate.

3. The cation-selective electrode of claim 2, wherein said counter-anion of said cation exchange material is an alkylated naphthalene sulfonate.

4. The cation-selective electrode of claim 3, wherein said counter-anion of said cation exchange material is dinonylnaphthalene sulfonate.

5. The cation-selective electrode of claim 3, wherein said counter-anion of said cation exchange material is didodecylnaphthalene sulfonate.

6. The cation-selective electrode of claim 1, wherein the cationic moiety of said cation exchange material comprises said organic cationic species whose measurement is desired.

7. The cation-selective electrode of claim 6, wherein said organic cationic species present in said cation exchange material is an organo-substituted ammonium cation.

8. The cation-selective electrode of claim 6, wherein said organic cationic species present in said cation exchange material is a quaternary ammonium cation.

9. The cation-selective electrode of claim 6, wherein said organic cationic species present in said cation exchange material is an alkaloidal cation.

10. The cation-selective electrode of claim 6, wherein said organic cationic species present in said cation exchange material is the protonated form of phencyclidine.

11. The cation-selective electrode of claim 6, wherein said organic cationic species present in said cation exchange material is the protonated form of propranolol.

12. The cation-selective electrode of claim 1, wherein said membrane is formed as a coating directly on a conductive substrate.

13. The cation-selective electrode of claim 12, wherein said conductive substrate is in the form of a conductive wire.

14. The cation-selective electrode of claim 1, wherein said membrane is in electrical contact with an internal reference electrode element through an internal reference electrolyte solution.

15. In a process for measuring the concentration of a large organic cationic species in an aqueous test solution as a function of potentiometric response employing a cation-selective electrode, the improvement which comprises employing the cation-selective electrode as defined in claim 1, whereby the concentration of said large organic cationic species in the test solution may be measured with a high degree of selectivity with respect to both smaller organic cationic species and inorganic cationic species.

16. The process of claim 15, wherein the counter-anion of the cation exchange material present in the membrane component of said cation-selective electrode is an alkylated naphthalene sulfonate.

17. The process of claim 15, wherein the cationic moiety of the cation exchange material present in the membrane component of said cation-selective electrode comprises said large organic cationic species whose measurement is desired.

18. The process of claim 17, wherein said large organic cationic species is an organo-substituted ammonium cation.

19. The process of claim 17, wherein said large organic cationic species is a quaternary ammonium cation.

20. The process of claim 17, wherein said large organic cationic species is an alkaloidal cation.

21. The process of claim 17, wherein said large organic cationic species is the protonated form of phencyclidine.

22. The process of claim 17, wherein said large organic cationic species is the protonated form of propranolol.

* * * * *